United States Patent [19]

Burbank

[11] Patent Number: 5,114,407
[45] Date of Patent: May 19, 1992

[54] SAFETY MECHANISM FOR TROCAR

[75] Inventor: John E. Burbank, Ridgefield, Conn.

[73] Assignee: Ethicon, Inc., Somerville, N.J.

[21] Appl. No.: 575,245

[22] Filed: Aug. 30, 1990

[51] Int. Cl.⁵ ............................................... A61M 5/18
[52] U.S. Cl. ...................................... 604/164; 606/185
[58] Field of Search ............... 604/164, 165, 272, 273, 604/274; 606/185

[56] References Cited

U.S. PATENT DOCUMENTS

| | | | |
|---|---|---|---|
| 4,535,773 | 8/1985 | Yoon | 604/51 |
| 4,601,710 | 7/1986 | Moll | 604/165 |
| 4,650,030 | 3/1987 | Moll et al. | 604/165 |
| 4,902,280 | 2/1990 | Lander | 604/165 |
| 5,030,206 | 7/1991 | Lander | 606/185 X |

FOREIGN PATENT DOCUMENTS

WO89/03661 5/1989 European Pat. Off. .

*Primary Examiner*—Michael H. Thaler
*Attorney, Agent, or Firm*—Paul A. Coletti

[57] ABSTRACT

A safety trocar is provided which includes a spring-loaded shield that shields the cutting tip of the obturator after the obturator penetrates tissue. The distal end of the shield is hemispheric in profile and contains a slot which conforms to the geometry of the cutting tip. Instead of using a discrete shield component the shielding function may be provided by spring-loading the trocar tube itself to spring forward and shield the obturator tip after the tip penetrates tissue. Alternately a safety mechanism insures the tip is covered by the shield after the tip penetrates tissue.

9 Claims, 16 Drawing Sheets

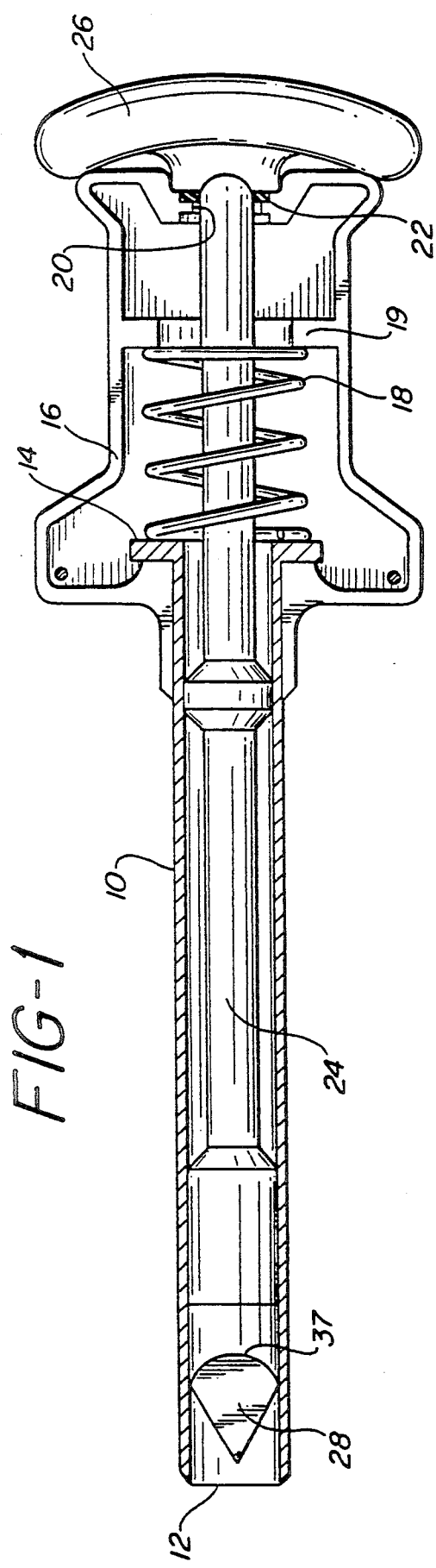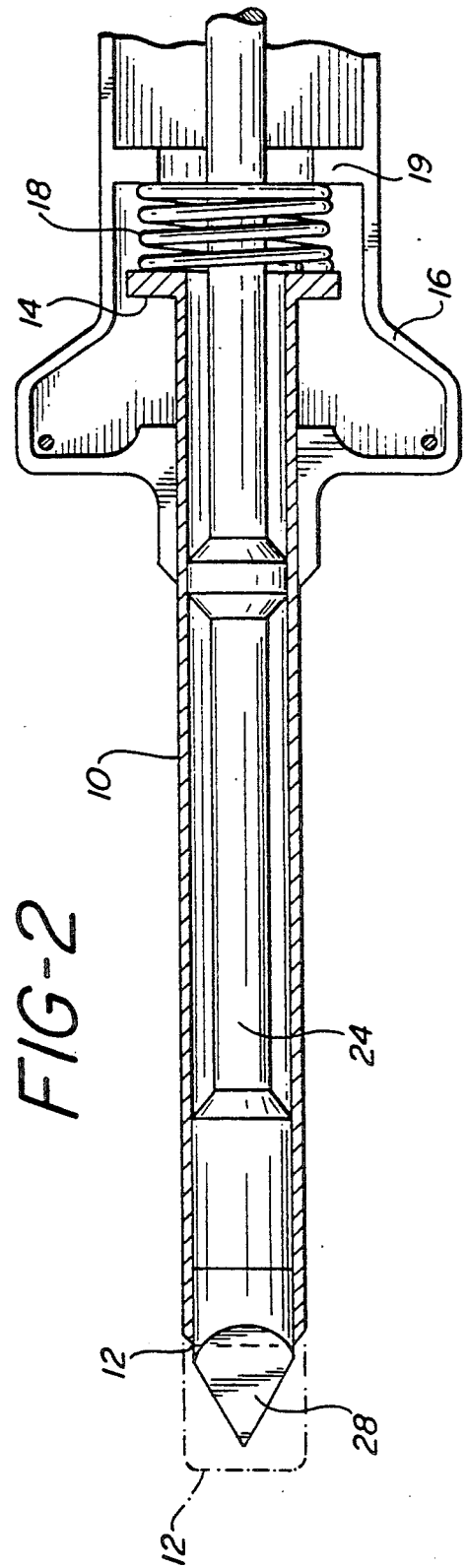
FIG-1
FIG-2

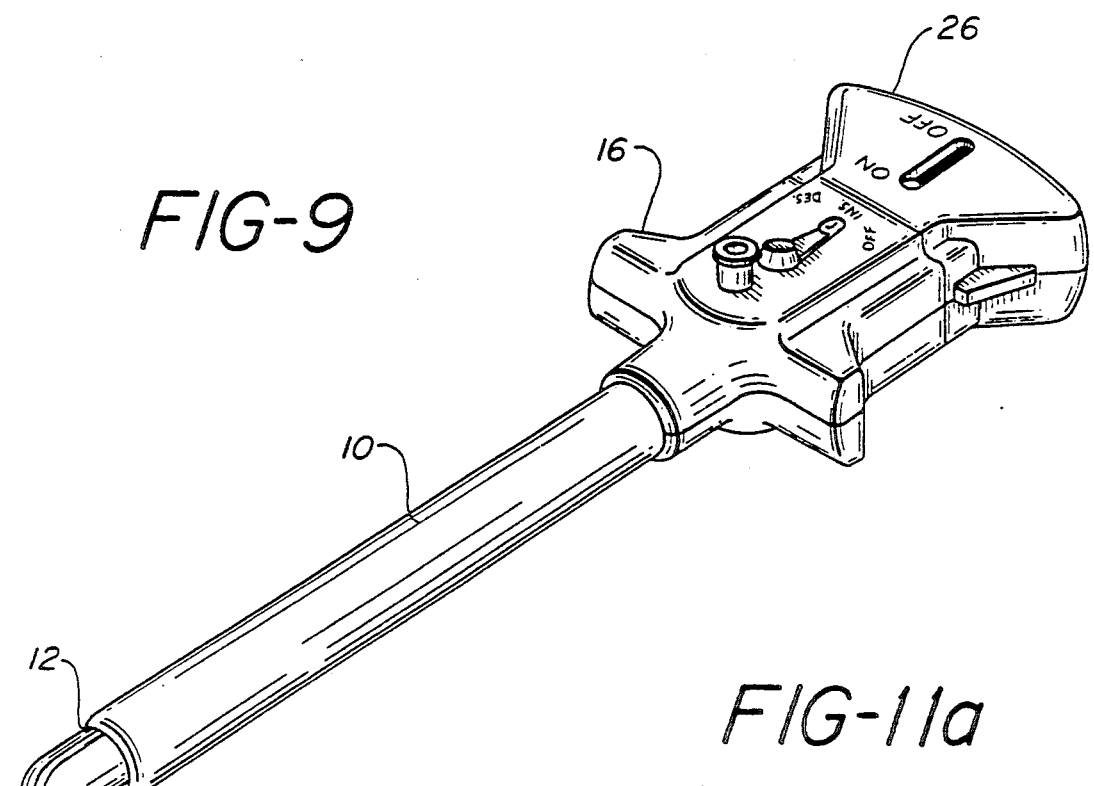
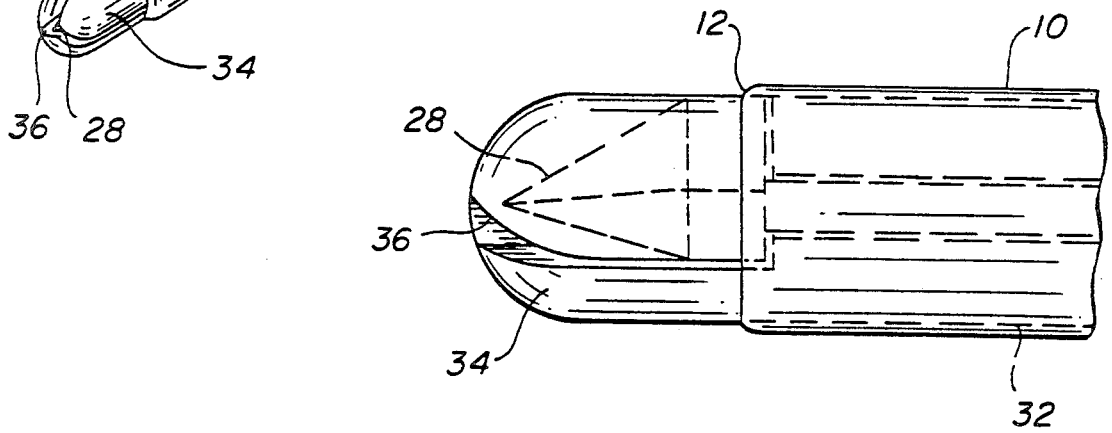
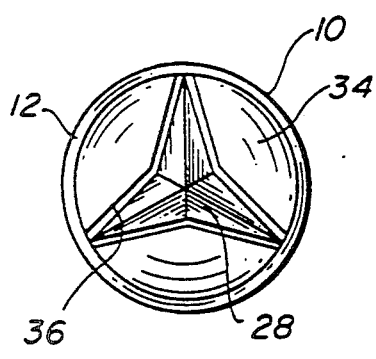
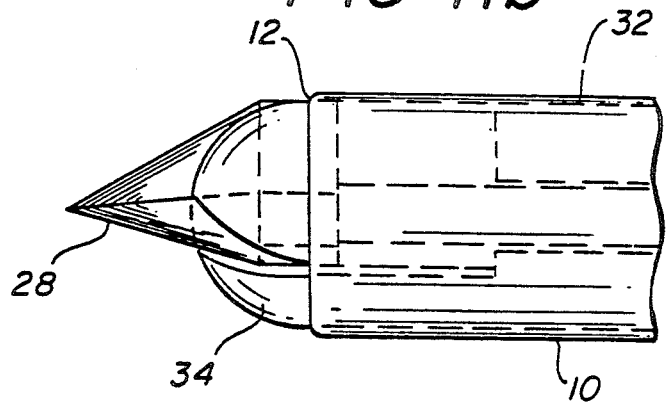

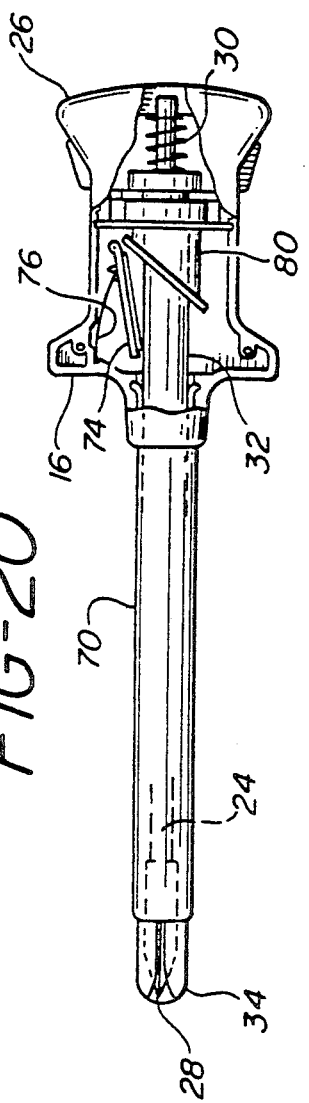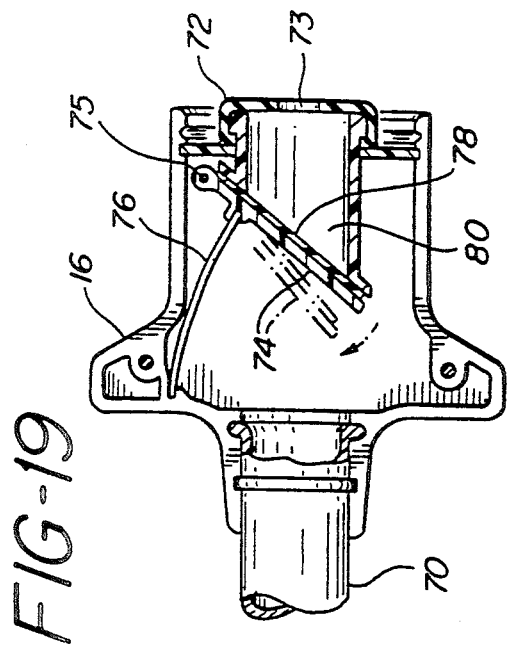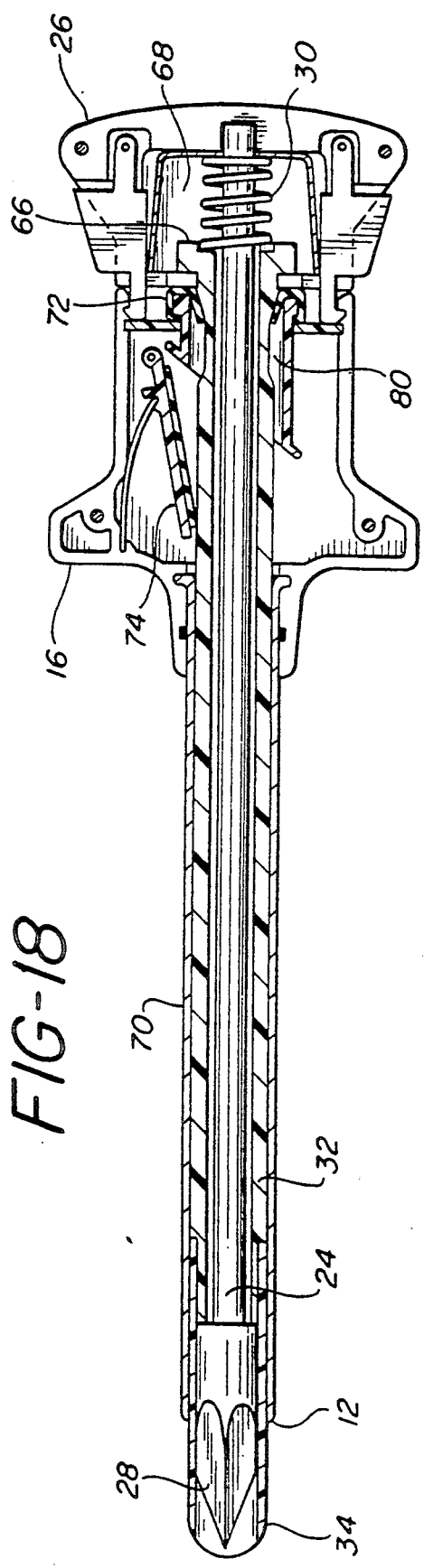

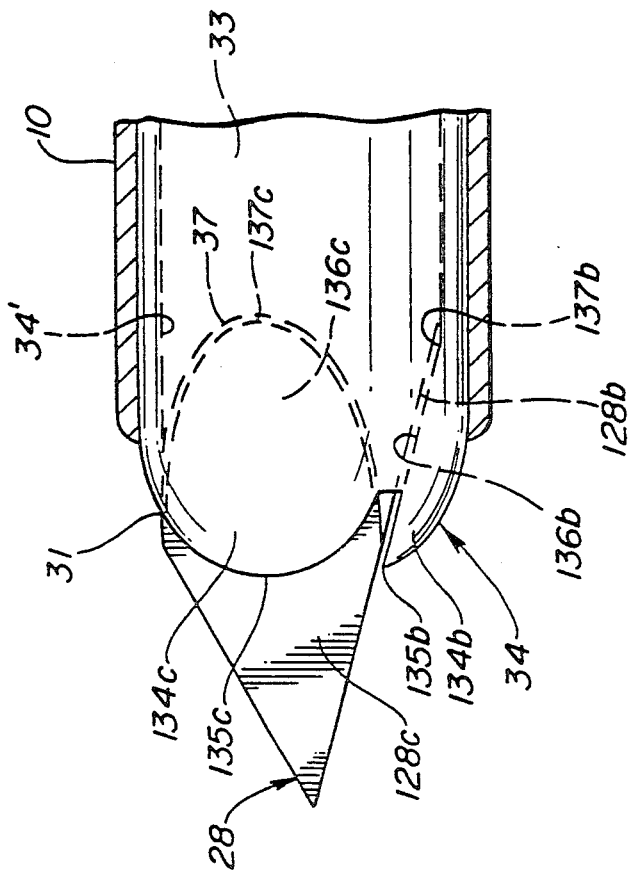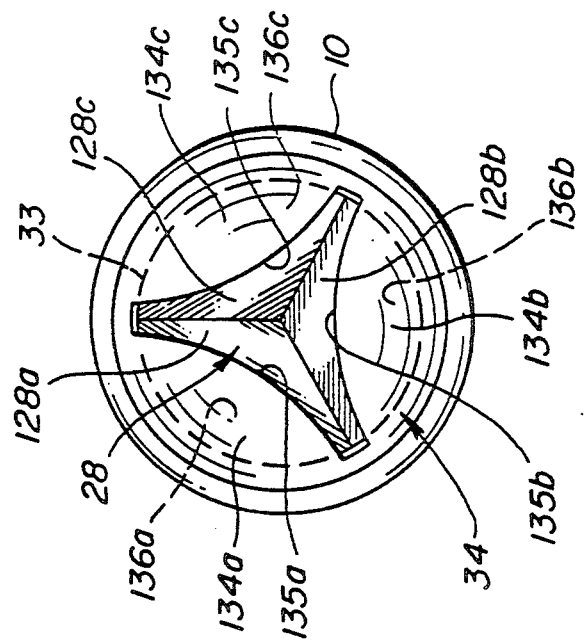

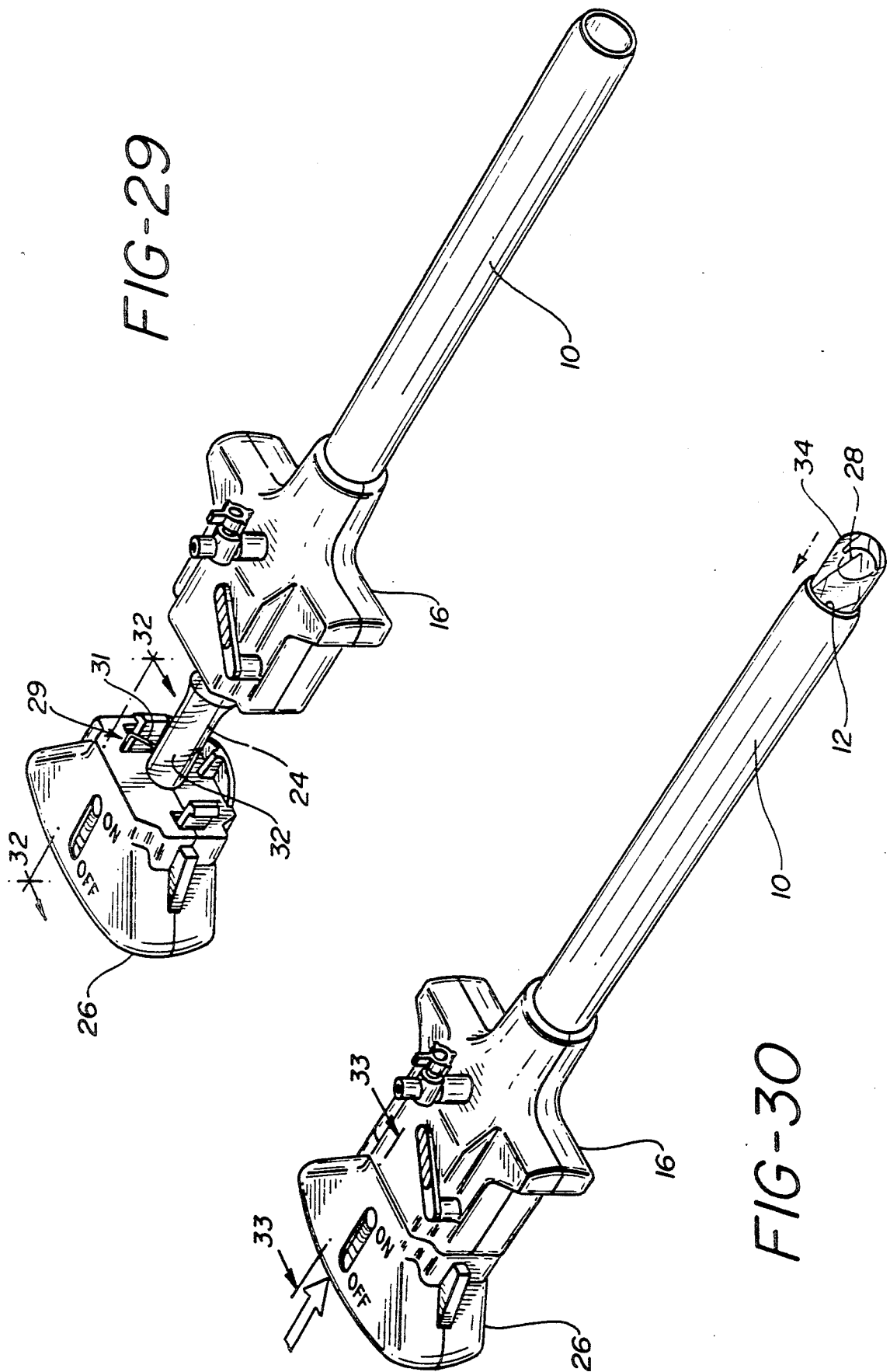

SAFETY MECHANISM FOR TROCAR

This invention relates to trocars used to puncture tissue for the performance of laparoscopic or arthroscopic surgery and, in particular, to such trocars which employ a safety device to shield the obturator point immediately after the point has perforated tissue.

A trocar generally comprises two major components, a trocar tube and an obturator. The trocar tube is inserted through the skin to access a body cavity through the tube in which laparoscopic or arthroscopic surgery is to be performed. In order to penetrate the skin, the distal end of the trocar tube is placed against the skin and an obturator is inserted through the tube. By pressing against the proximal end of the obturator the point of the obturator is forced through the skin until it enters the body cavity. At this time the trocar tube is inserted through the perforation made by the obturator and the obturator is withdrawn, leaving the trocar tube as an accessway to the body cavity.

It has been found that often a great deal of force is required to cause the obturator point to penetrate the skin and underlying tissue. When the point finally breaks through this tissue, resistance to penetration is suddenly removed, and the obturator point can suddenly penetrate to reach internal organs of the body, which may cause lacerations and other injury to the internal organs. To avert this danger to the patient, trocars have been developed which carry a spring-loaded tubular shield within the trocar tube and surrounding the obturator. The distal end of the shield will press against the skin as the obturator point penetrates the body until the obturator has formed a perforation with a diameter sufficient to allow the shield to pass through. At that time the resistance of the tissue to the spring-loaded shield is removed, and the shield will spring forward to extend into the body cavity, surrounding the point of the obturator. The shield thus protects the internal body organs from inadvertent contact with the point of the obturator. A trocar including such a safety shield is described in U.S. Pat. No. 4,535,773, for example.

The tubular shield in such a trocar will, however, require the incision formed by the obturator to extend to a considerable diameter before the resistance of the tissue pressure has been sufficiently decreased to allow the safety shield to spring forward. It is only when the incision attains the diameter of the shield that the shield is fully able to spring into the body cavity. When the obturator employs a long, tapered cutting tip, this tip must extend a significant distance into the body before the incision is sufficiently enlarged to release the safety shield. It would therefore be desirable to provide a safety shield which will spring forward to shield the obturator tip as soon as possible after entry is gained to the body cavity.

In accordance with the principles of the present invention, a safety shield for a trocar obturator is provided which exhibits a rounded, bullet-shaped distal end. A slot is formed in this distal end which corresponds to the geometry of the obturator tip, through which the tip extends during perforation of the skin. With this distal end conforming to the geometry of the tip, a smooth transition is provided from the tip to the distal end of the shield, enabling the shield to closely follow the obturator tip through the tissue. The rounded distal end will press against the skin and tissue in close proximity to the periphery of the incision as it is formed, and will aid in the enlargement of the incision to enable the shield to spring forward as soon as entry is gained into the body cavity.

It is desirable for the obturator to slide smoothly within the trocar tube during both insertion and retraction of the obturator. Opposing this desire is the need to form the obturator to be nearly the same diameter as the tube, so that the perforation will be the size of the tube. Thus, tolerances are generally tight between the outside diameter of the obturator and the inside diameter of the trocar tube. Further complication is provided by the valve at the proximal end of the trocar tube, which is needed to seal the proximal end during removal of the obturator when the trocar tube and body cavity are insufflated with gases. The valve, which generally takes the form of a hinged flap or trumpet valve, is spring-loaded to bear against the obturator, thereby assuring that the valve will close automatically upon withdrawal of the obturator of the tube. As the valve bears against the obturator it will frictionally disrupt the entry and withdrawal of the obturator, and at times can even jam and lock the obturator within the trocar tube.

In accordance with a further aspect of the present invention, the valve within the proximal end of the trocar tube is oriented at an acute angle with respect to the trocar tube when the valve is closed. Ease of entry of the obturator or any endoscopic instrument is afforded when the shielded tip of the obturator or instrument presses against the angularly disposed valve, and the angular orientation minimizes jamming of the obturator or instrument and valve within the trocar. In a preferred embodiment the valve is manually controllable in discrete positions for insufflation, desufflation, and valve closure in concert with the operation of a gas fitting.

Further patient safety would be provided by preventing the sudden extension of the obturator into the body cavity as the obturator tip fully penetrates the tissue. In accordance with yet another aspect of the present invention, means are provided which permits only incremental advancement of the obturator as tissue penetration proceeds. Such incremental advancement is provided by a ratchet or screw mechanism, for instance.

It would further be desirable to provide the safety of the trocar with the safety shield, but in a device which reduces the component complexity of the trocar and tube with the spring-loaded safety shield. In accordance with still another aspect of the present invention, the trocar tube is spring-loaded and employed as the safety shield. Thus, as the obturator point breaks through the tissue, the trocar tube will spring forward automatically into the body cavity, thereby providing shielding about the tip of the obturator. A safety mechanism holds the shield over the tip.

In the drawings:

FIGS. 1–4 illustrate the use of the trocar tube to provide shielding of the obturator tip;

FIGS. 9–11b and 18 illustrate operation of a trocar with a bullet nosed shield;

FIGS. 19-21 illustrate a trocar with an angularly disposed valve at the proximal end of the trocar tube;

FIGS. 27 and 28 illustrate an obturator and shield which requires only a short extension of the obturator from the distal end of the shield;

FIG. 29 is a perspective view of a trocar assembly containing a safety mechanism as described in the present invention, with the actuation means of the safety mechanism exposed;

FIG. 30 is a persepective view of a closed trocar with the trocar shield covering the obturator tip;

Figure 3:
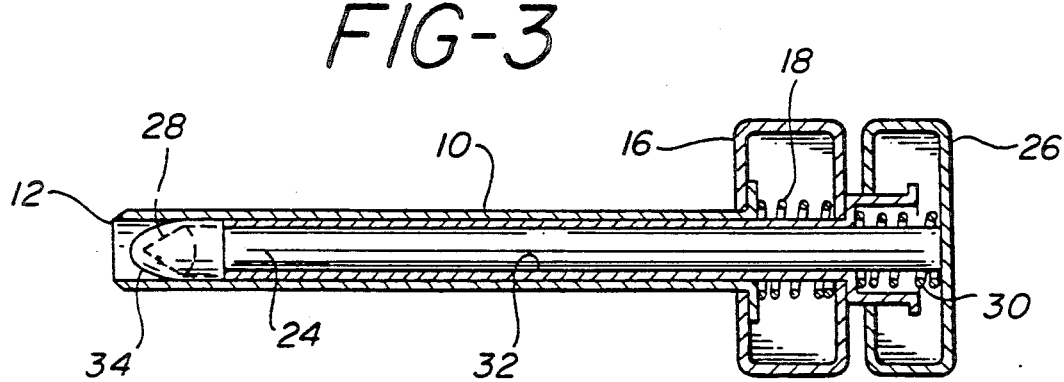

A safety trocar constructed in accordance with the principles of the present invention is shown in FIG. 1. The trocar includes a trocar tube or cannula 10 having an open distal end 12 and an open, flanged proximal end 14. The proximal end 14 is mounted in a trocar handle 16. A spring 18 is located inside the handle and abuts the flanged end of the trocar cannula 10 and a stop 19 within the handle 16. There is an aperture 20 at the proximal end of the handle 16 which is surrounded by a gasket ring 22.

An obturator 24 is slideably and removeably located within the trocar cannula and is inserted into the handle and trocar cannula by way of the aperture 20. At its proximal end is an obturator handle 26, and the distal end of the obturator is sharpened to a point 28. The safety trocar of FIG. 1 is used to puncture a hole in soft tissue by placing the distal end 12 of the trocar cannula 10 against the tissue, and pressing against the obturator handle 26. As pressure is exerted against the obturator handle, the trocar cannula 10 begins to compress the spring 18 inside the trocar handle 16 and the trocar cannula retracts into the handle 16. This retraction of the trocar cannula exposes the obturator point 28, which punctures the tissue. FIG. 2 shows the spring 18 fully compressed within the trocar handle 16 and the obturator point 28 fully exposed beyond the distal end 12 of the trocar cannula. When the obturator point 28 breaks through the inner surface of the tissue, the spring-loaded trocar cannula 10 will spring forward around the obturator 24, shielding the obturator point to prevent inadvertent contact of the point with internal organs of the body inside the tissue being punctured.

Figure 5A:
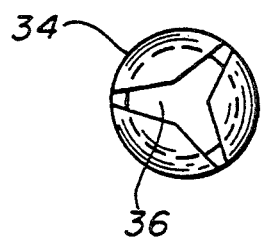
FIGS. 5a–8 illustrate a trocar safety shield with a bullet-shaped nose.

FIG. 3 shows a safety trocar in which like reference numerals refer to the elements previously described in FIG. 1. In FIG. 3 the obturator 24 is enclosed in a bullet nosed obturator shield 32. The obturator shield 32 is flanged at its proximal end to engage a spring 30 within the obturator handle 26. At its distal end the obturator shield has a slotted bullet-shaped nose 34. An end view of the bullet nose 34 is shown in FIG. 5a, with its slot 36. The slot 36 is seen to extend radially to the outer periphery of the bullet nose at the distal end of the obturator shield 32. In FIG. 3 the springs 18 and 30 are shown in their uncompressed positions.

Figure 4:
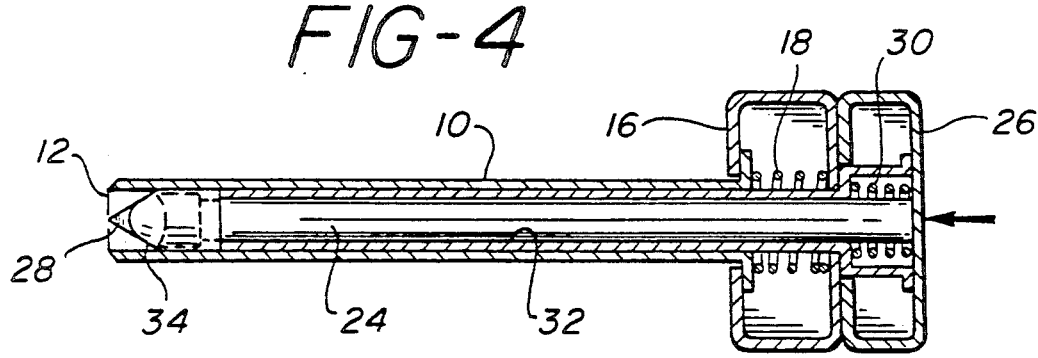
Figure 5B:
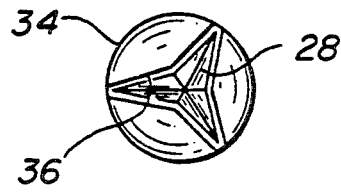

When pressure is initially exerted at the obturator handle 26, the spring 30 within the obturator handle compresses, as shown in FIG. 4. This compression of the spring 30 causes the obturator point 28 to extend beyond the bullet nose 34 of the shield through the slot 36, as shown in FIG. 5b. Further exertion of pressure at the handle 26 will cause the trocar cannula to compress the spring 18, and the obturator point will then begin to extend out the distal end 12 of the trocar cannula 10. The extended obturator point will then puncture the tissue at the distal end of the trocar cannula until the point breaks through the inner surface of the tissue. At that time the resistance at the distal end of the trocar will be removed, and the spring 18 will extend the trocar cannula 10 forward about the point 28 of the obturator. When the obturator and obturator handle are withdrawn from the trocar cannula, the bullet nosed shield will continue to protect the point of the obturator after it has been used. The spring-loaded trocar cannula 10 provides protection against accidental puncture of an organ within the body, and the shield 12 continues to provide protection against user injury after the obturator is withdrawn from the trocar cannula.

Figure 6:
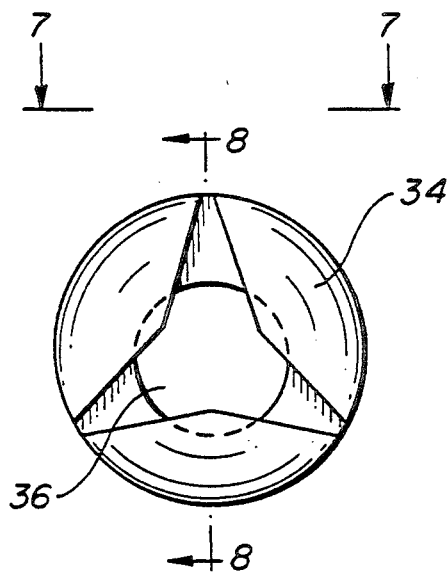
Figure 7:
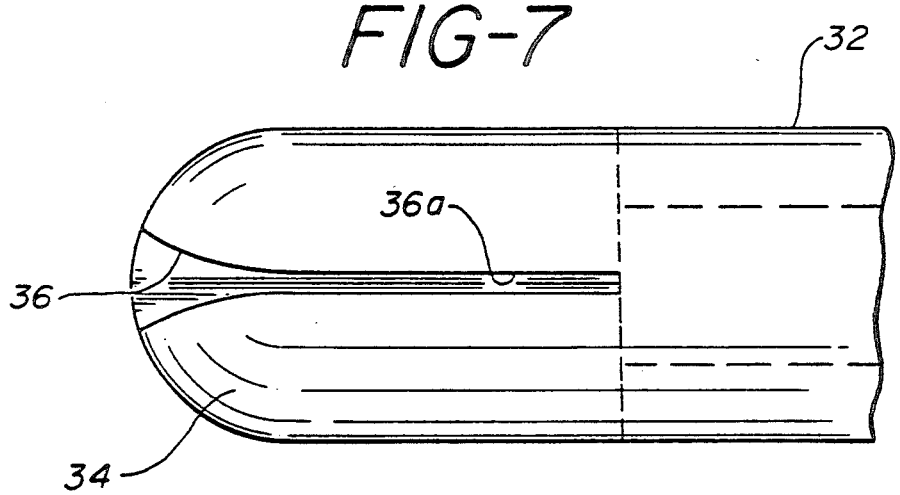
Figure 8:
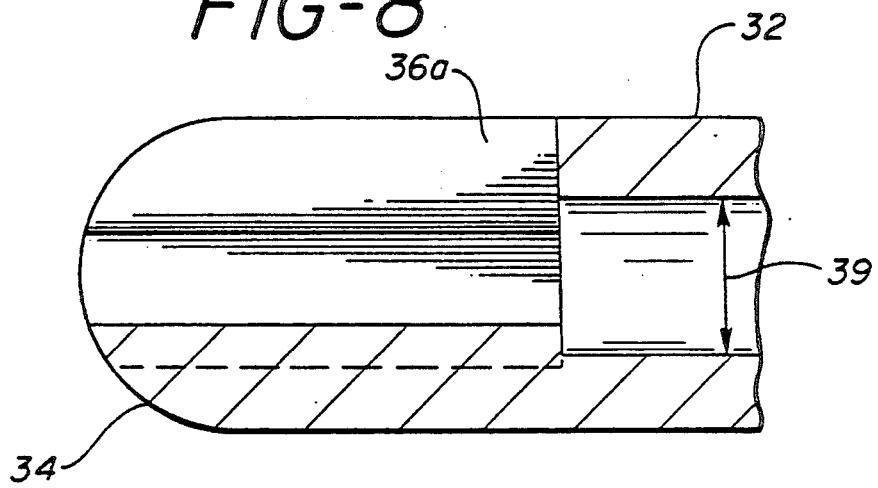

The bullet nosed end 34 of the shield 32 is shown in enlarged views in FIGS. 6-8. FIG. 6 shows an enlarged end view of the bullet nose 34 with a star-shaped slot 36. In the side view of FIG. 7, the slot 36 is seen to extend toward the rear of the shield as indicated at 36a. The sharpened edges of the star-shaped obturator point will thus extend radially through slots 36a to the outer perimeter of the shield, and will hence cut a puncture the same diameter as the outer diameter of the shield 32. When the puncture is the same size as the shield, the shield is enabled to readily spring forward to protect the point of the obturator as it breaks through the inner surface of the tissue. The cross-sectional view of the bullet nose 34 in FIG. 8 shows the rearward extension of the slot 36a in which the edges of the obturator point slide, and the widened inner diameter 39 within the shield proximal the nose for the shaft of the obturator. The bullet nose 34 of the shield aids penetration through the punctured tissue and improves the blending between the obturator facets and the cannula, thereby improving the responsiveness of the spring-loaded cannula.

Operation of the trocar with bullet nosed shield of FIGS. 3-8 is shown in FIGS. 9-11. FIG. 9 is a perspective view of the trocar with the trocar cannula 10 compressed inside the trocar handle 16 so that the bullet nose 34 of the shield extends from the distal end 12 of the trocar cannula. An end view of the distal end of the instrument is shown in FIG. 10. FIG. 11a is an enlarged side view of the distal end of the instrument of FIG. 9, with the bullet nose 34 extended and the star-shaped obturator point 28 still retracted within the shield. In FIG. 11b the obturator point 28 is shown extended from the slot 36 of the bullet nose 34.

Figure 12A:
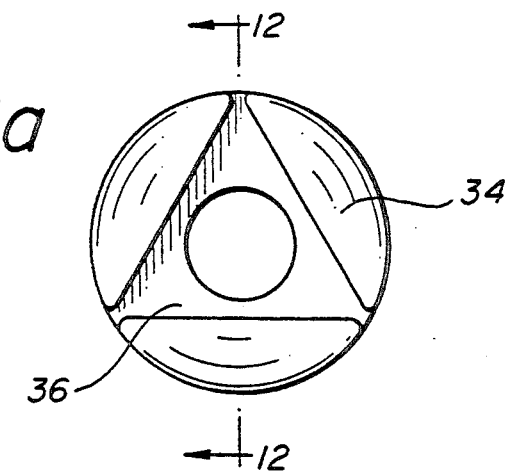
FIGS. 12–12d illustrate a bullet nosed safety shield when used with a triangular-pointed obturator.
Figure 12:
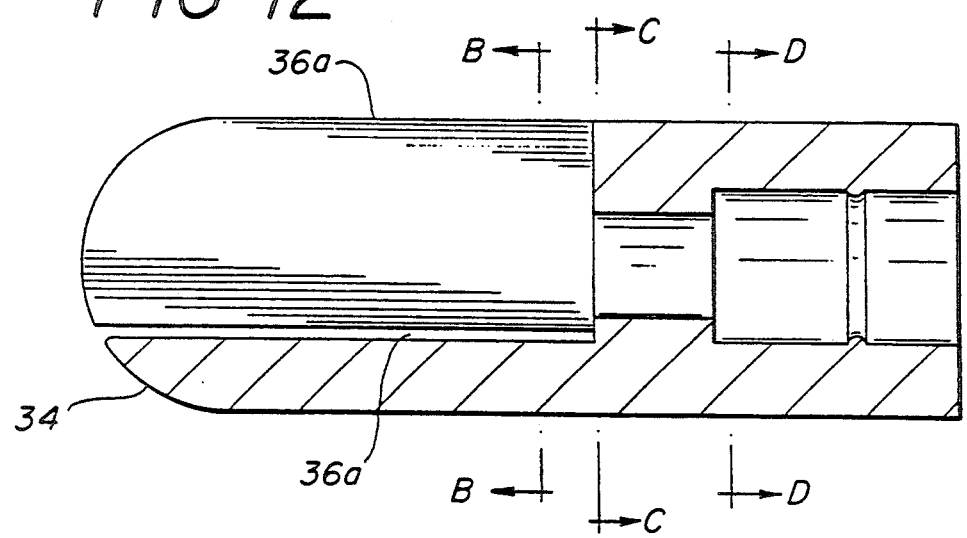
Figure 12B:
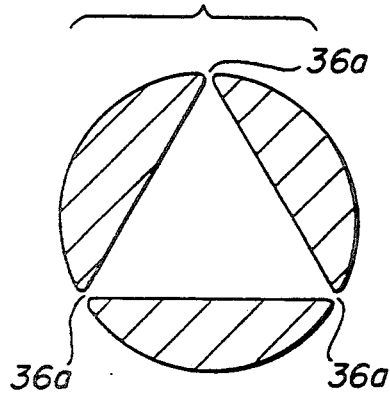
Figure 12C:
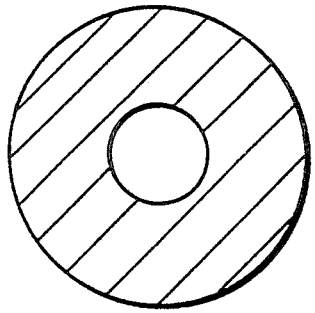
Figure 12D:
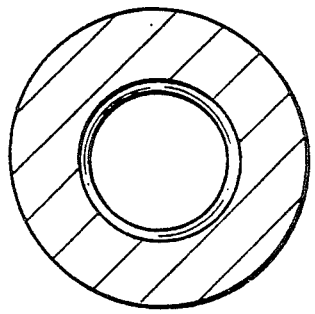

FIGS. 12-12d are similar to FIGS. 6-8, and show the bullet nose 34 of the shield 32 when used with a triangular-pointed obturator. FIG. 12 shows the bullet nose 34 in cross-section, with slot 36a extending along the side of the shield. FIG. 12a is a view of the distal end of the bullet nose, showing the triangular slot 36 extending to the periphery of the shield. FIGS. 12b, 12c, and 12d are cross-sectional views taken as indicated for areas B, C, and D of FIG. 12.

Figure 13:
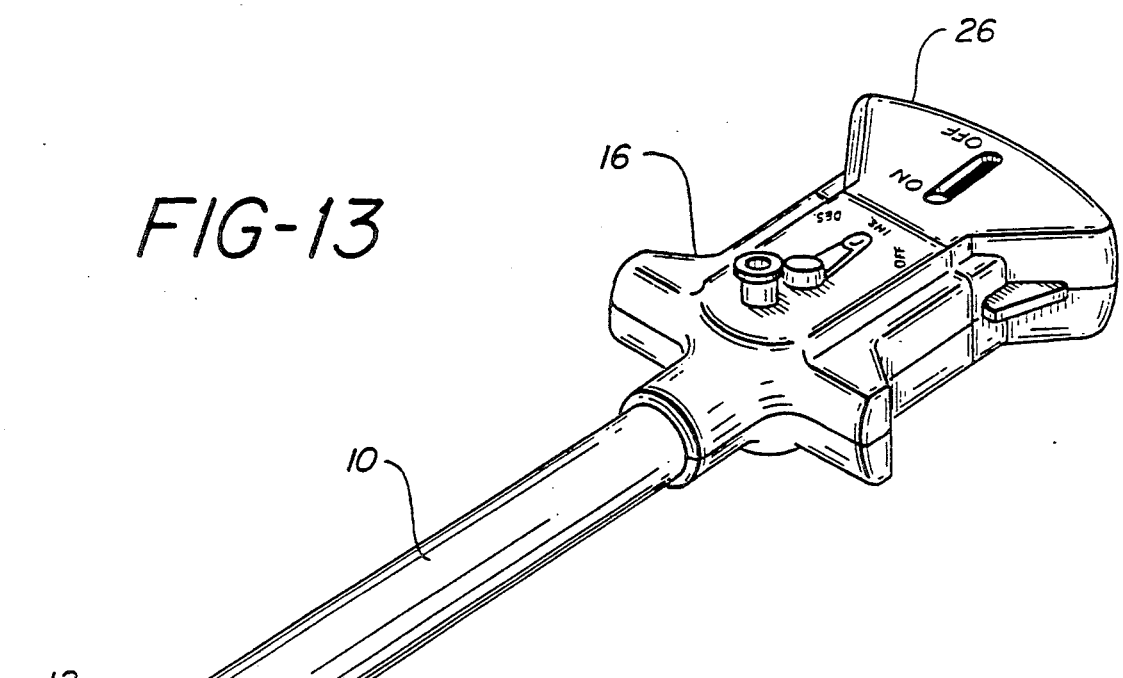
FIGS. 13–15b illustrate operation of a trocar with a bullet nosed shield and a triangular-pointed obturator.
Figure 15A:
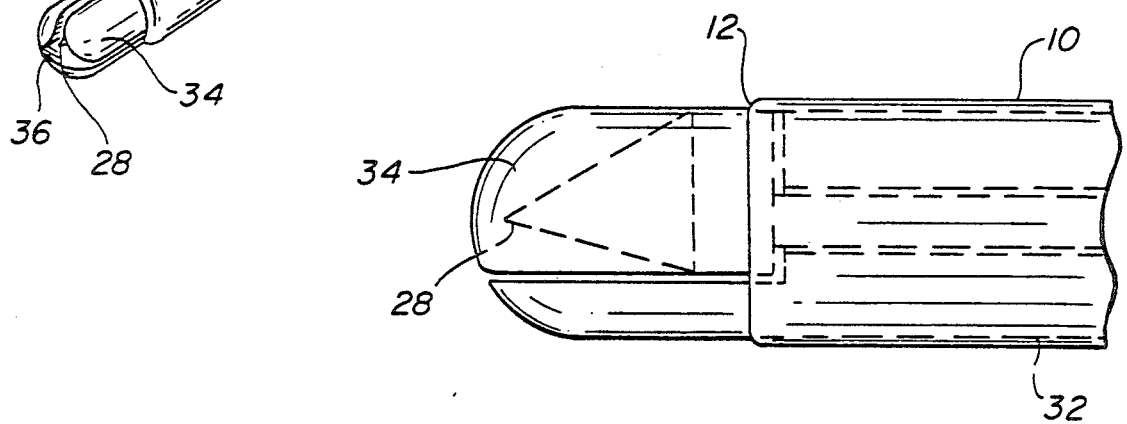
Figure 14:
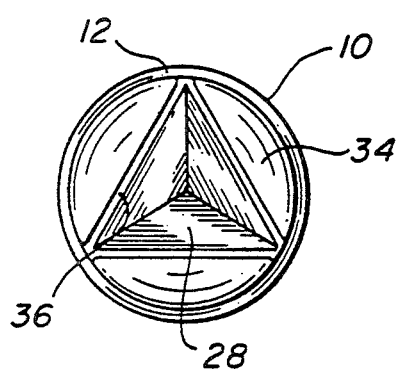
Figure 15B:
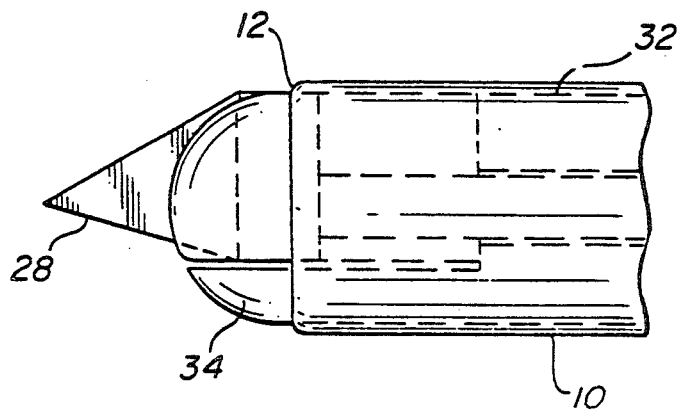

Operation of the trocar with a triangular pointed obturator is as shown in FIGS. 13-15b. FIG. 13 is a perspective view of the trocar, with the trocar cannula pressed into the handle 16 to reveal the bullet nose 34 of the shield at the distal end 12 of the trocar cannula. The indicator on the obturator handle is in the "on" position, indicating to the user that the obturator point 28 is retracted within the bullet nosed shield 32. FIG. 14 shows the distal end of the instrument and the trianglar point 28 of the obturator within the triangular slot 36. FIG. 15a shows the bullet nose 34 of the shield 32 entending beyond the distal end 12 of the trocar cannula 10, with the obturator point 28 still within the bullet nose 34. FIG. 15b shows the obturator point 28 in its extended position. It may be seen that the edge 29 of the obturator point 28 is fully extended to the outer periphery of the bullet nosed shield 32 so as to cut a puncture of the same diameter as that of the shield. The three semi-circular fingers of the rounded bullet nose 34 will then fold the three opposing flaps of tissue aside as the shield 32 springs forward around the obturator point 28 when the puncture is made. In addition there is less trauma to the skin caused by pressing the rounded bullet nose fingers against the tissue as compared to the trauma caused by a tube-like shield.

An embodiment of an obturator and shield which requires only a short extension of the obturator point is shown in FIGS. 27 and 28. In this embodiment there are no slots 36a extending along the sides of the shield from the end slot 36. Instead, the obturator point 28 cuts only to a radial dimension 31 at the outer edges of the point, within the inner diameter 34' of the shield. In prior art instruments which cut to this radius, the obturator point must be extended out of the shield to the blend 37 of the point 28 and the round shaft 33 of the obturator. In the illustrated embodiment, the obturator point 28 need be extended only half this distance from the bullet nosed shield 34 in order to achieve a cut of the full point diameter.

In the embodiment of FIGS. 27 and 28 the hemispheric bullet-shaped nose of the shield is seen to comprise three distal lobes, 134a, 134b, and 134c, each with a semicircular distal end 135a, 135b, and 135c which define the slot through which the obturator point 28 extends. The triangular pyramidal obturator tip 28 has three substantially flat surfaces or faces 128a, 128b, and 128c which are ground to blend into the cylindrical shaft 33 of the obturator as shown at 37. FIG. 28 shows that each lobe 134a, 134b, and 134c is thickened to have a substantially flat inner surface 136a, 136b, 136c, one of which is shown in this FIGURE. This inner surface contacts and fits against the proximal surface of the corresponding face of the obturator tip when the tip is fully extended, at which time the proximal edge 137a, 137b, 137c of each thickened lobe is substantially aligned with the blend 37 of each face. Thus, the geometry of the bullet-shaped nose is closely aligned with that of the obturator tip, and the lobes will fit against the faces of the tip and follow the tip into the perforation as it is cut by the tip. The lobes will spread the edges of the perforation to accommodate the bullet-nosed shield and the shield will then spring forward to protect the obturator tip as soon as the tip breaks through the tissue.

Figure 16:
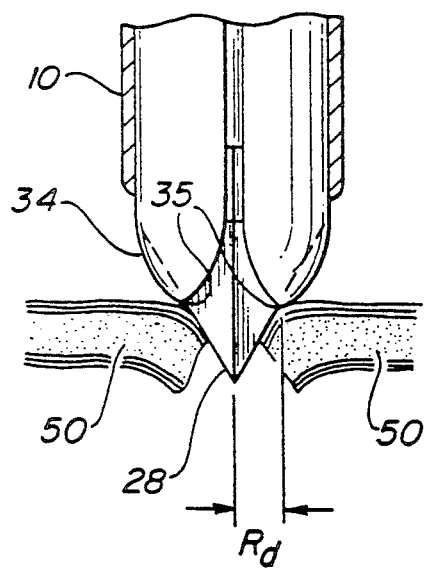
FIGS. 16 and 17 illustrate the penetration of tissue by a trocar with a bullet nosed safety shield.
Figure 17:
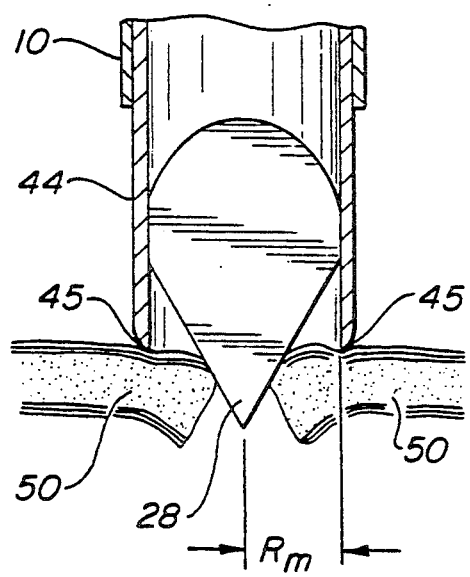

FIGS. 16 and 17 compare operation of the safety trocar of the present invention with that of prior instruments. Both FIGURES show trocars in operation just as the obturator tip breaks through the tissue 50. FIG. 17 illustrates operation of known instruments, in which the shield for the obturator point is a tubular shield 44. This shield engages the tissue being punctured as shown at 45. This shield is not able to overcome the tissue resistance at 45 and spring forward to protect the obturator point until the obturator has made a puncture with a radius as indicated by $R_m$. When this occurs, the obturator point 28 is already well within the body and may have already damaged organs inside the body. By comparison, the bullet nosed shield 34 contacts the tissue outside the puncture site at points indicated at 35 in FIG. 16. These contact points are at a much smaller radius $R_d$ from the obturator point 28. This smaller radius, together with the spherical shape of the nose 34, enable the bullet nosed shield to spring forward through the puncture at a much earlier time than the prior tubular shield, thereby protecting the point 28 of the obturator as soon as it breaks through the tissue.

By virtue of this superior protective action, a trocar can be made to rely solely on the protective action of the spring-loaded shield 34 without the spring-loaded trocar cannula. An embodiment of this type is shown in FIG. 18. The trocar cannula 70 is attached at its proximal end to the cannula handle 16. The obturator shield 32 and obturator 24 slide within the trocar cannula 70. A flange 66 at the proximal end of the shield 32 engages the spring 30, and is slideably engaged within a passageway 68 in the obturator handle 26. The bullet nose 34 of the shield is shown extended beyond the distal end 12 of the trocar cannula, but with the obturator point 28 still retracted within the shield. As the spring 30 is compressed when the bullet nose 34 contacts the tissue being punctured, the obturator point 28 will extend beyond the bullet nose and puncture the tissue. Once the point has broken through the tissue, the bullet nosed shield 32 will spring through the puncture to shield the point 28 within the body.

Figure 21:
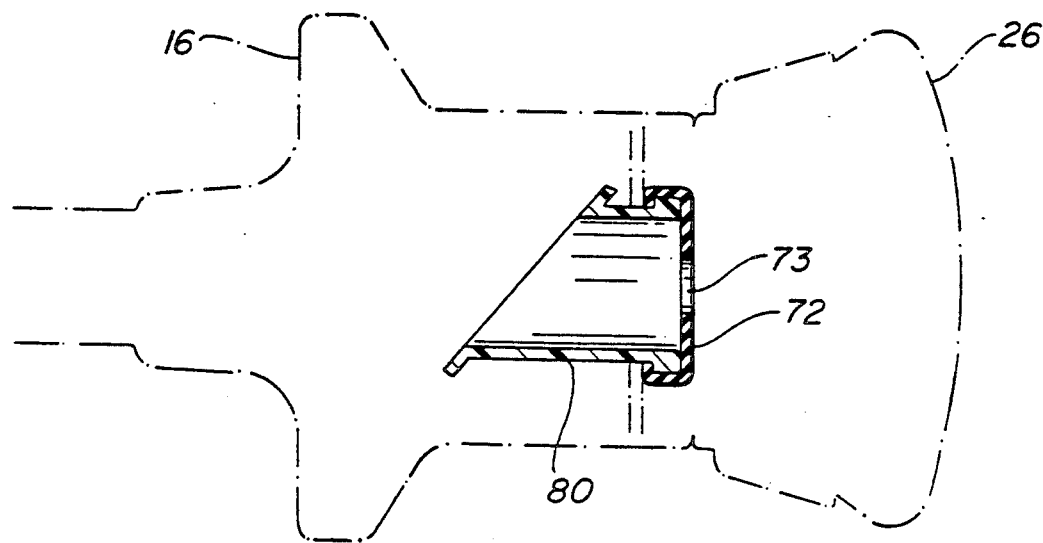

Prior to and after retraction of the obturator from the body, the body at the puncture site is generally insufflated with air. To prevent the air from escaping through the puncture, the trocar cannula and handle are generally equipped with a valve mechanism to prevent air leakage. FIG. 19 is a cross-sectional view of the trocar handle 16, showing a proximal tubular passageway 80 which is angled at its distal end. At the distal end of the passageway 80 is a flap valve 74 which is hinged at 75. A rubber-like sealing pad 78 is located on the side of the flap valve which contacts the distal end of the passageway 80. At the proximal end of the passageway 80 is a replaceable gasket 72 which has an aperture 73. The use of gaskets with different diameter apertures permits the trocar to be used with instruments of many different sizes. The internal diameter of the passageway 80 is sized to allow the shield 32 to smoothly slide through the passageway with the gasket 72 providing a seal around the shield. FIG. 21 shows an enlarged view of the trocar handle 16, the obturator handle 26, the passageway 80, and the gasket 72.

FIG. 20 shows the shield 32 and obturator 24 completely inserted within the trocar cannula 70. After the puncture is made, the shield 32 and obturator 24 are withdrawn from the trocar cannula 70, and the flap valve 74 swings shut against the distal end of the passageway 80 as the shield 32 clears the distal end of the passageway. The flap valve swings closed under the force of a spring 76. The distal end of the passageway 80 is thus securely sealed against air leakage while the shield is still sealing the proximal end of the passageway 80 at the gasket 72. The angled distal end of the passageway 80 permits the flap valve to be easily pushed open by the shield, or any endoscope instrument and prevents the shield from becoming jammed between the sealing pad 78 and the passageway as the flap valve closes. The distance between the flap valve 74 and the proximal gasket 72 ensures that the valve will be completely closed before the shield is removed from the gasket. Additionally the design of the trocar of FIG. 20 enables a user to selectively expose the obturator point or retract it into the shield.

Figure 22:
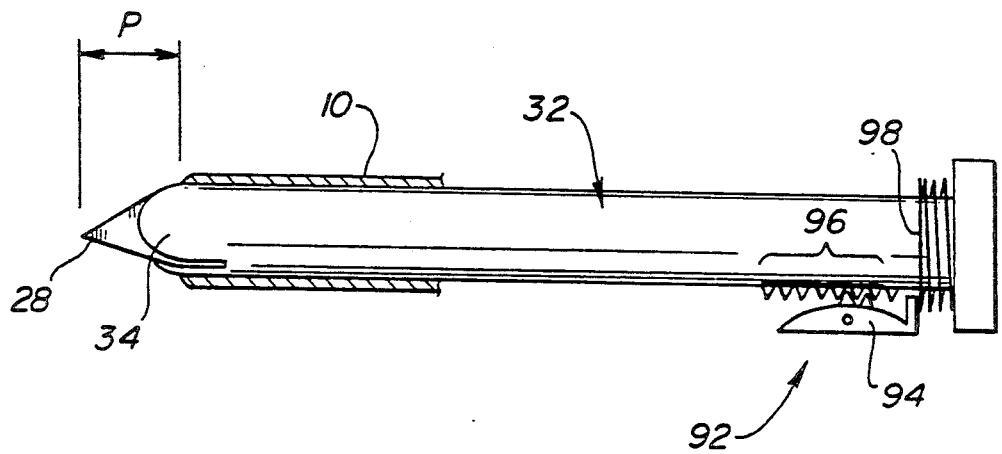
FIG. 22 illustrates apparatus for permitting only incremental advancement of the obturator of a trocar.

During some surgical procedures, a substantial amount of force is required to cause the obturator to puncture the tissue. The sudden release of back pressure as the puncture is achieved often causes the obturator to burst through the tissue and injure organs within the body. FIG. 22 shows a trocar which prevents this sudden breakthrough and extension into the body. Located within the obturator handle 26 is a mechanism 92 connected to the obturator or shield 32 which permits only incremental advancement of the obturator. In FIG. 22 this mechanism 92 is illustrated as a pivoting toothed cam 94, which engages matching teeth 96 on the shield 32. A return spring 98 is connected to the proximal end of the cam 94 so that the mechanism 92 will exhibit a ratchet-like operation, permitting extension of the obturator in small incremental distances. The mechanism 92 permits the obturator to be extended only a total distance "P" into the body, which is sufficient to provide a puncture of the desired diameter. The ratchet mechanism 92 is only illustrative of the types of mechanisms that may be employed. Other suitable mechanisms include a linear or rotary double pawl clock escapement, or a coarse pitch screwing action whereby the obturator is incrementally advanced as the obturator handle is turned. Either these or other suitable mechanisms will permit only incremental advancement of the obturator while providing tactile feedback to the surgeon indicating that the obturator is being advanced through the tissue.

As seen in FIGS. 29 through 36, there is also disclosed a safety mechanism useful in maintaining the tip 34 of shield 32 covered over the preforating tip 28 of the obturator. This safety mechanism is generally seen in the perspective view of FIG. 29. There is an actuating spring 31, forming the safety mechanism 29, capable of placing the safety mechanism into positon. As seen in FIG. 30, the safety mechanism is in position, and will be actuated by the movement of the tip 34 of safety shield 32 away from the perforating tip 28 of the obturator.

Figure 31:
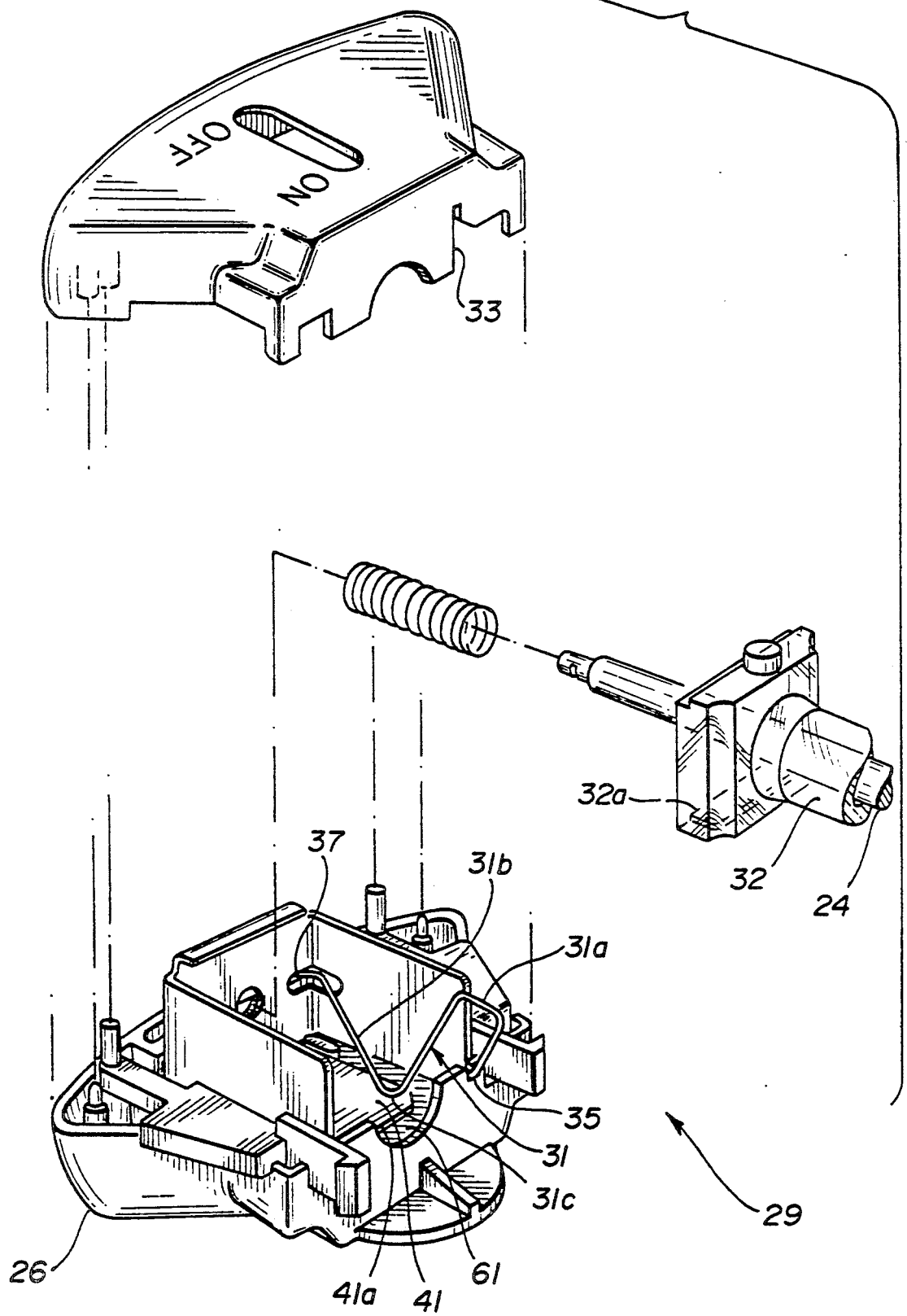
FIG. 31 is an exploded view of the safety mechanism employed in the present invention.
Figure 32:
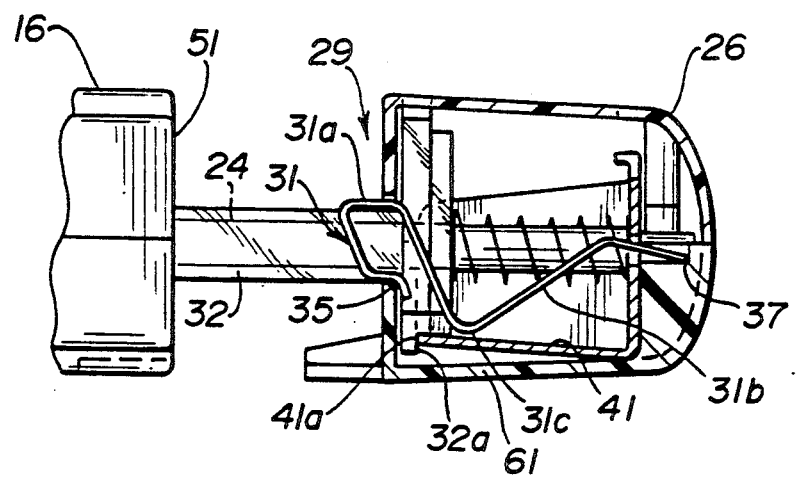
FIG. 32 is a cross-sectional taken across the lines 32-32 of FIG. 29.
Figure 33:
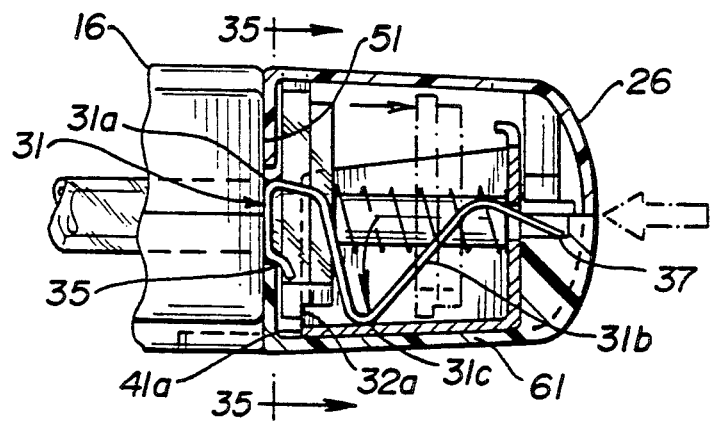
FIG. 33 is a cross-sectional view of the closed trocar mechanism as taken across the lines 33-33 in FIG. 30.
Figure 34:
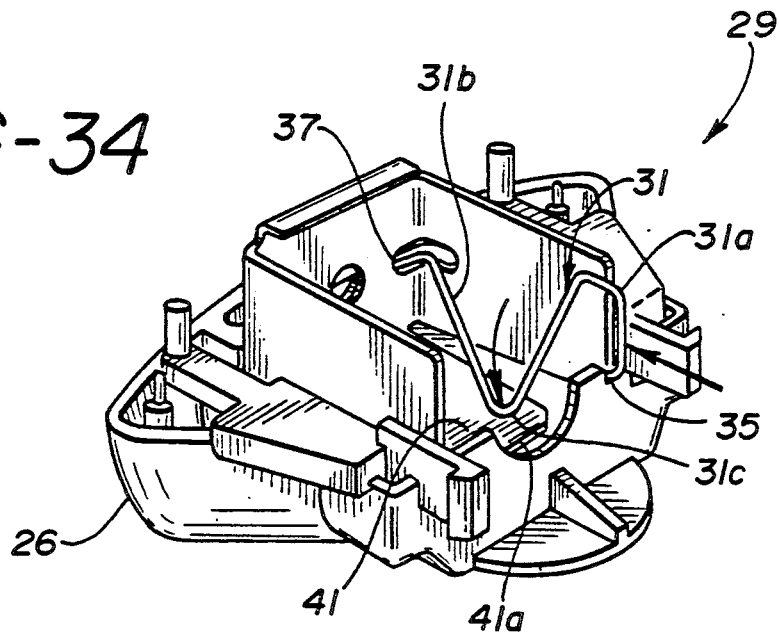
FIG. 34 is a partial assembly view of the handle of the trocar mechanism.
Figure 35:
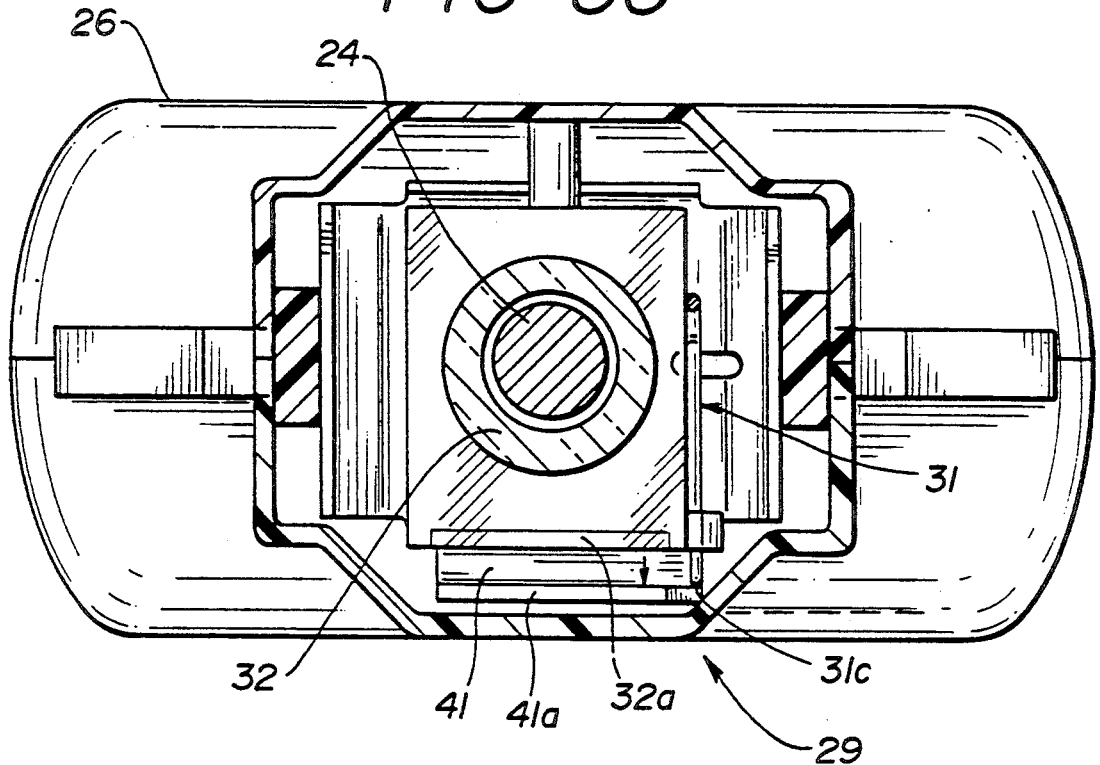
FIG. 35 is a cross-sectional view of the handle taken across lines 35—35 of FIG. 29.

As seen in FIG. 31 there is an exploded view of the handle containing the safety mechanism as described in the present invention. A safety mechanism 29 capable of keeping the shield 32 in place over the obturator 24 is disclosed. This mechanism 29 comprises an "S"-shaped retainment or safety spring 31 which moves within slot 33. Spring 31 is pivoted at points 35, 37 so that spring 31 rotates about points 35 and 37. The geometry of spring 31 is controlled so that there is rotation of lower section 31a about an axis which runs generally perpendicular to obturator 24 and rotation of upper section 31b about an axis parallel to obturator 24. This is controlled in part by the ground point 37 and slot 33 which cause upper portion 31b to carefully rotate toward obturator 24. When the handle is closed, the tip of the one portion of the handle contacts the safety spring 31 as seen in FIG. 32, this compresses the safety spring 31 as seen in FIG. 33. As better seen in FIGS. 35 and 36, the S-shaped spring 31 is also able to rotate from the plate 41 and within the confines of the handle 16. Thus, although spring 31 is not fixed in any one position, it allows for motion of plate 41 in order to actuate the safety mechanism.

This "S"-shaped spring 31 helps to keep obturator 24 covered by shield 32 when obturator 24 has been inserted into the body. Specifically, edge 51 of cannular handle 16 forces spring 31 to rotate within slot 33 and into obturator handle 26. An edge of upper portion 31b contacts securement plate 41 and rotates plate 41 toward the back wall 61 of obturator handle 26. This plate 41 is better seen in the cross-sectional view of FIGS. 32 and 33. Securement plate 41 therefore ceases to block rim 32a of shield 32. Obturator 24 pierces the skin with shield 32 held behind the obturator 24 as the spring force against spring 30 is overcome by the body. As shield 32 moves to the rear of the instrument, rim 32a rotates spring corner 31c away from its position against locking plate 41. After piercing the skin, the force of spring 30 now is greater than the patient's resistive force. Therefore shield 32 is urged over obturator 24. In so doing, rim 32a of shield 32 slides into contact with edge 41a of locking plate 41, which now unobstructed has rotated back into place, and plates 41 therefore prevents rearward motion of shield 32. Thus, plate 41 prevents the inadvertent exposure of obturator 24, until the instrument is opened and spring 31 again is activated. This occurs by the rotation of spring 31 into its original position, ready to rotate plate 41 away from shield 32.

Figure 36:
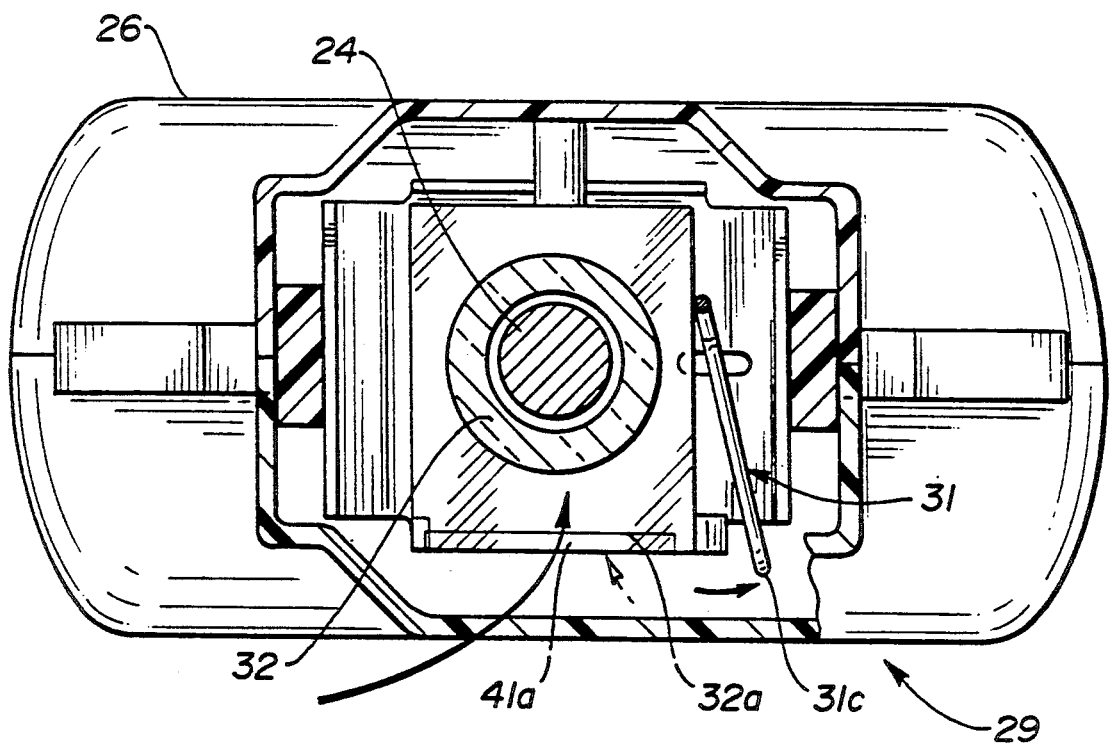
FIG. 36 is a cross-sectional view of the handle as taken across lines 36—36 of FIG. 30.

Thus, as seen in the dynamic FIGS. 29, 30, 32, 33, 35 and 36, the plate 41 originally is in the path of the safety shield 32 and is held against the rim 32a of the safety shield 32. Thus, first the spring 31 is held in position as in FIG. 32, such that the spring 31 is exposed to the handle 16 and the plate 41 is held against the rim of the shield so that the shield 32 covers the obturator 24, and the shield 32 is not able to be telescoped within the handle 16 end. When the handle 16 is closed as is FIG. 33, the spring 31 causes the plate 41 to be rotated out of the position of holding against the rim 32a of the shield 32 so that the shield may be telescoped within the handle. When this happens, the spring 31 is also caused to rotate from its position in FIG. 35 to its position in FIG. 36. When this happens, the spring 31 is no longer able to block the path of the plate 41, as best seen in FIG. 36. Also, once the spring 31 is moved out of the way, there is no possibility of the spring 31 being able to overcome the rim 32a of the shield.

Thus, after obturation, and the movement of the shield over the tip, the plate 41 is now free to be moved back into position as in FIG. 32. The spring 31 is no longer able to hold the plate 41 away from motion of the shield 32, and the shield 32 is therefore held in place. The handle 16 must be open from cannula handle 26 in order for the retainment spring 31 to be able to be reactivated so that the plate 41 can again be used.

FIGS. 23-26 illustrate a control on the trocar handle for enabling regulation of the insufflation of the body. The control includes a pivotally mounted lever 100 located on the top of the trocar handle 16. The lever 100 is moveable to three discrete positions: off, insufflate, and desufflate. At a position just forward of the lever 100 is an insufflation fitting 102, located over a passageway 108 which leads to the interior of the handle 16.

Connected to the pivot shaft 104 of the lever is a key 106, which pivots with the lever.

Figure 24:
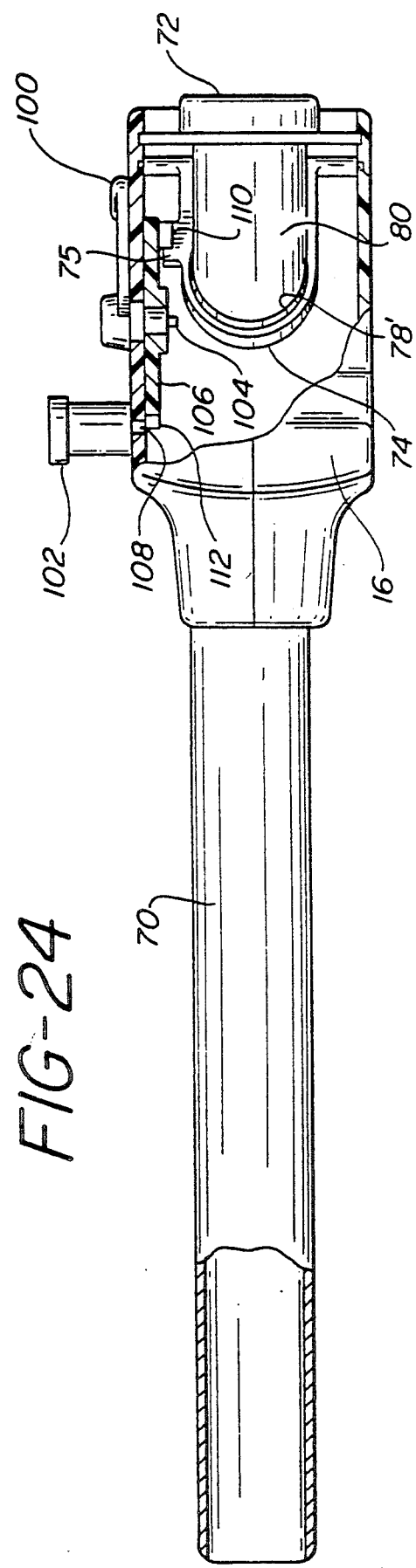
Figure 25:
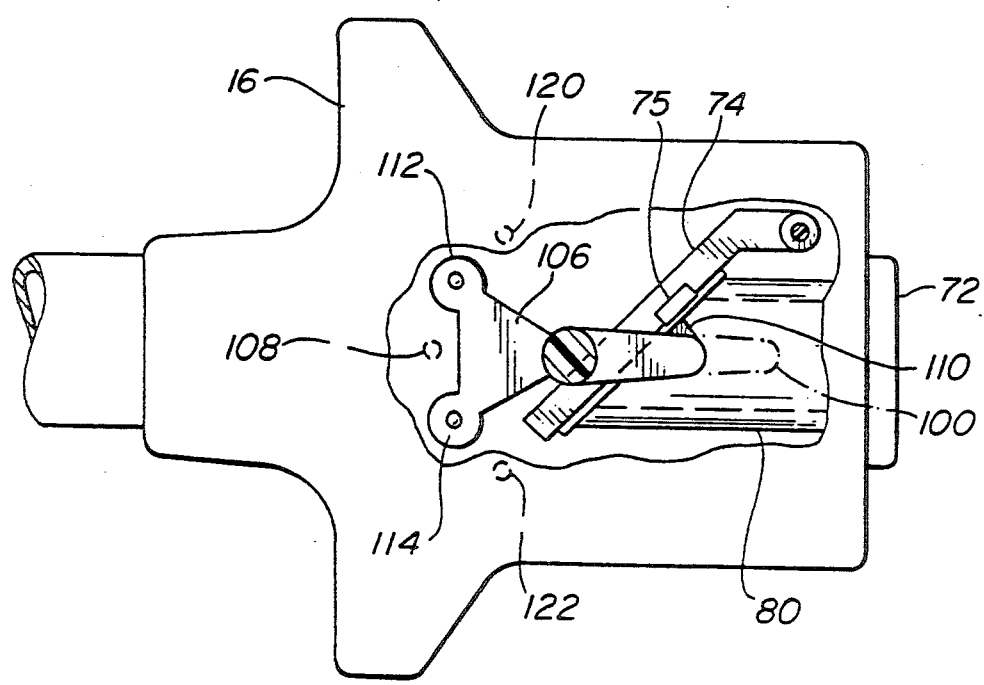

FIG. 25 is a plan view of the handle 16 with the top of the handle removed. In this view the key 106 is seen to have two ears 112 and 114, each with an upward extending central dimple. As the key is rotated with the lever, the dimples trace an arc along the top of the handle. Located in this arc of travel are the passageway 108 and two depressions 120 and 122, which act as detent positions for the dimples on the key ears 112 and 114. Located on the proximal extension of the key 106 is a pointer 110, which opposes an upward extension 75 of the flap valve 74 within the handle 16 (see FIG. 24). FIG. 24 illustrates that the angled distal end of the passageway 80 may have its own circular gasket 78' located around the distal end of the passageway.

When the lever 100 is rotated to the "off" position, the dimple on the key ear 112 clicks into the depression 120 and the dimple on the key ear 114 fits into the inner end of the insufflation passageway 108, thereby sealing the passageway. With the passageway 108 sealed, pressurized air inside the trocar cannula 70, the trocar handle 16 and the body will not leak out of the insufflation fitting. The flap valve 74 seals the distal end of the passageway 80 at this time.

Figure 23:
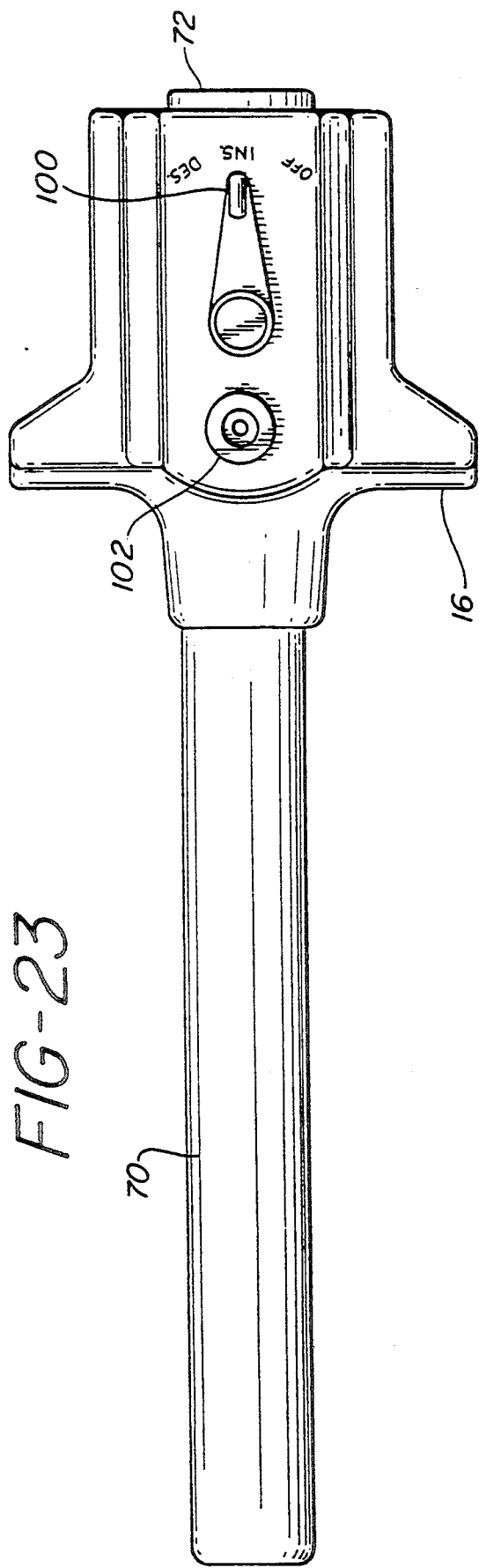
FIGS. 23-26 illustrate a control on a trocar for regulating insufflation of the body.
Figure 26:
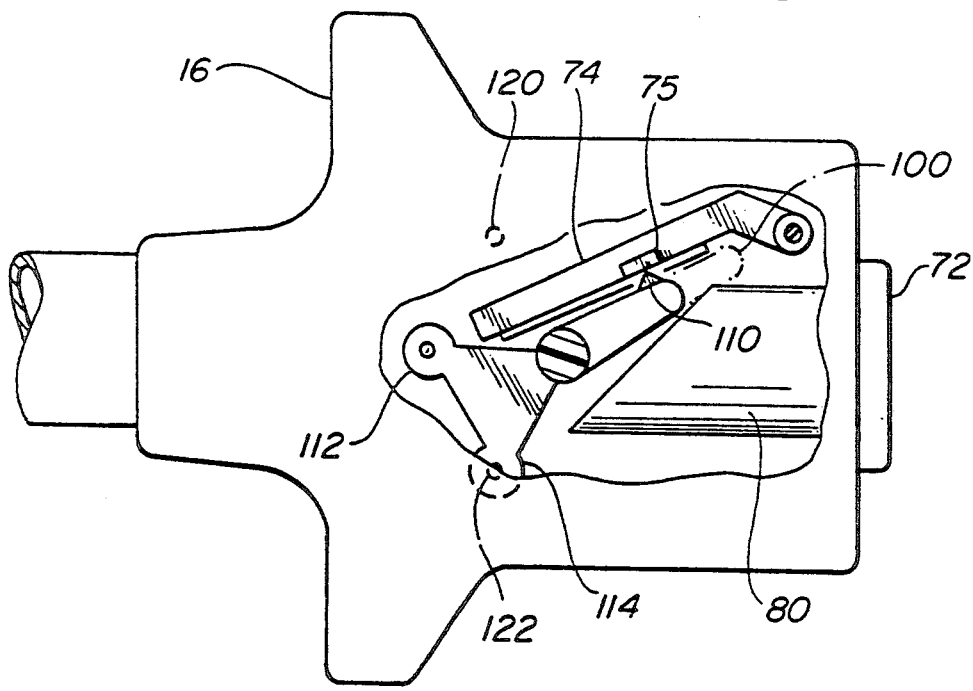

When it is desired to insufflate the body, a source of pressurized gas is connected to the insufflation fitting 102 and the lever is moved to the "insufflate" position as shown in FIGS. 23, 24, and 25. In this position the passageway 108 is not blocked by the key 106 and pressurized gas may enter the interior of the handle and the trocar cannula through the insufflation fitting 102, insufflating the body. After the body has been properly insufflated with gas, the lever 100 may be moved back to the "off" position to seal the pressurized gas in the trocar, and the gas source may be removed from the fitting 102. When it is desired to desufflate the body, the lever 100 is pivoted to the "desufflate" position as shown in FIG. 26. The pivoting of the lever causes the key pointer 110 to contact the flap valve extension 75 and swing the flap valve away from its sealing position at the distal end of the passageway 80. Pressurized gas within the handle and trocar cannula will thus be vented through the passageway 80. As the key swings to its detent position the dimple on the key ear 114 clicks into the depression 122 and the dimple on the key ear 112 seals the passageway 108 to prevent the venting of air through the passageway 108 and the insufflation fitting 102.

What is claimed is:

1. A trocar comprising:
    a trocar tube having a proximal end and a distal end, said tube proximal end connected to a trocar handle;
    an obturator having a perforating tip and extendable through the tube to perforate tissue at the distal end of the tube;
    a safety shield extendable to shield the tip of the obturator, said safety shield exhibiting a rounded distal end with a slot for passage of said obturator tip therethrough; and
    wherein said shield and obturator are connected to a handle having a top and a bottom, and said handle comprising:
    a first spring;
    a securement plate for maintaining said shield and said obturator in a closed position wherein said shield encloses said obturator, said securement plate movable by said first spring into an open position wherein said obturator tip may be exposed; and
    wherein said first spring comprises a retainment spring, said retainment spring pivoted about a pair of points on said handle such that when in said open position said retainment spring contacts said plate, and in said closed position said retainment spring rotates out of the path of said plate.

2. The trocar of claim 1 wherein said shield has a rim located within said handle and said securement plate is rotatable within said handle to contact said rim in said closed position.

3. The trocar of claim 2 wherein said shield is spring-loaded by a second spring attached to said handle.

4. The trocar of claim 3 wherein in said open position, said plate is held out of the path of said shield rim by said first spring to permit free movement of said shield, and said second spring urges said shield over said obturator tip such that a force must overcome said second spring force to urge said shield toward said handle to expose said tip.

5. The trocar of claim 1 wherein said retainment spring is generally "S"-shaped.

6. The trocar of claim 5 wherein said handle has a slot on its bottom surface and said retainment spring moves within said slot, said retainment spring extending past said handle bottom surface in its recovered position.

7. The trocar of claim 6 wherein said retainment spring contacts said trocar tube handle and such contact rotates said retainment spring into said handle such that said spring contacts said plate to urge said plate into the open position.

8. The trocar of claim 7 wherein said retainment spring is urged out of the path of said shield by said shield rim in order to place said shield into the closed position.

9. The trocar of claim 8 wherein said retainment spring remains in the closed position until said trocar tube is removed from contact with said retainment spring.

* * * * *